United States Patent
Astle

(10) Patent No.: US 7,270,789 B1
(45) Date of Patent: Sep. 18, 2007

(54) PIPETTOR HEAD HAVING STANDPIPES OPEN AT THEIR TOPS TO A PRESSURE/VACUUM CHAMBER AND METHOD

(76) Inventor: Thomas W. Astle, 607 Harborview Rd., Orange, CT (US) 06477

( * ) Notice: Subject to any disclaimer, the term of this patent is extended or adjusted under 35 U.S.C. 154(b) by 806 days.

(21) Appl. No.: 10/799,613

(22) Filed: Mar. 15, 2004

(51) Int. Cl.
*B01L 3/02* (2006.01)

(52) U.S. Cl. .................. 422/100; 422/63; 422/67; 422/68.1; 422/81; 422/103; 435/52; 435/54; 435/180; 73/863.73; 73/864.16; 73/864.17; 73/863.32

(58) Field of Classification Search .............. 422/63, 422/67, 68.1, 81, 100; 435/52, 54, 180; 73/863.1, 73/863.73, 864.15, 864.16, 864.17, 863.32
See application file for complete search history.

(56) References Cited

U.S. PATENT DOCUMENTS

| | | | | |
|---|---|---|---|---|
| 6,150,158 | A * | 11/2000 | Bhide et al. ............ | 435/286.3 |
| 6,372,185 | B1 * | 4/2002 | Shumate et al. ........ | 422/100 |
| 6,506,611 | B2 * | 1/2003 | Bienert et al. .......... | 436/180 |
| 6,637,476 | B2 * | 10/2003 | Massaro ................ | 141/237 |
| 2002/0142483 | A1 * | 10/2002 | Yao et al. .............. | 436/180 |
| 2002/0176801 | A1 * | 11/2002 | Giebler et al. ......... | 422/82.05 |
| 2003/0190264 | A1 * | 10/2003 | Yiu ..................... | 422/100 |

* cited by examiner

Primary Examiner—Walter D. Griffin
Assistant Examiner—Bobby Ramdhanie
(74) Attorney, Agent, or Firm—John H. Crozier

(57) ABSTRACT

In a preferred embodiment, a pipettor head, including: a body; one or more solenoid valves disposed in the body; each one or more solenoid valves having an outlet at a lower end and an inlet at an upper end; each one or more solenoid valves having an outlet attached to a dispensing passageway; each one or more solenoid valves having its inlet attached to a standpipe; and the standpipe having an open top communicating with an interior of a closed vacuum/pressure chamber defined in the pipettor head, the closed vacuum/pressure chamber being arranged such that vacuum or pressure may be selectively applied to the closed vacuum/pressure chamber. A method of using the pipettor head is also provided.

14 Claims, 9 Drawing Sheets

PIPETTOR HEAD HAVING STANDPIPES OPEN AT THEIR TOPS TO A PRESSURE/VACUUM CHAMBER AND METHOD

BACKGROUND OF THE INVENTION

1. Field of the Invention

The present invention relates to pipettor heads generally and, more particularly, but not by way of limitation, to a novel pipettor head and method of use in which each of the aspiration/dispensing needles therein is connected to an open top standpipe the top of which is disposed in a vacuum/pressure chamber to which vacuum or pressure may be selectively applied. A method of using the pipettor head is also provided.

2. Background Art

The pipettor head of the present invention may be used, for example, in the Quadra product line furnished by Tomtec Inc., of Hamden, Conn.

In the field of drug discovery for life science, there is a need for dispensing small aliquots of various reagents and biological materials. As the volume of testing increases, economics demands doing more with less. Scientific efforts have reduced the quantities of assay reagents required from milliliter quantities down to microliter quantities and lower. Instrumentation is required to maintain the required levels of accuracy and precision at these levels.

A wide variety of fluid delivery systems are in use. They include air displacement and positive displacement pipettor systems, single channel and multiple channels. In the nanoliter volume ranges, time/pressure systems using inkjet technology have found applications. This invention relates to this type of technology. A time pressure system simply opens a passageway allowing it to flow from a period of time. Controlling the open time combined with the head pressure, the volume dispensed can be controlled. Ink jet printing uses a fast acting, electronically activated, solenoid valve to open and close the flow path very quickly. A head pressure is applied to the flow path, which has a small orifice at the output end to create the backpressure required. If the head pressure is high enough to provide sufficient kinetic energy at the outlet orifice to overcome surface tension forces, small aliquots of liquid can be ejected in a non-contact mode. This is the principle of ink jet printing.

In ink jet printing, a common fluid, i.e. ink, is ejected. In the life science arena, multiple liquids must be transferred. This requires aspirating and dispensing. This can be accomplished by applying a negative pressure (vacuum source) instead of a positive pressure on the side of the valve opposite the orifice. This vacuum will cause liquid to move from the immersed orifice into a reservoir. Applying a positive pressure to the reservoir now reverses the direction of controlled flow. This type of technology is currently in use.

The conventional inkjet system, used for aspirating and dispensing, has a closed reservoir on one side of the fast acting solenoid valve and a small output orifice on the opposite side. Opening the valve, with the orifice immersed and a vacuum applied to the reservoir, will cause aspiration of the liquid into the reservoir. Closing the ink jet solenoid valve and applying positive pressure to the reservoir will reverse the action. This creates a dispense from the reservoir when the valve opens again.

In applications, such as life science, the reagents to be transferred are precious. Therefore dead volume, i.e. volume used to fill but cannot be used, is of concern. This requires the reservoir to be small in contained volume.

If multiple reagents are to be dispensed from the same flow path, there needs to be means of washing the flow path between reagents to prevent cross contamination. Commonly this is accomplished with multiple aspirating and dispensing functions with a suitable wash fluid. Due to the small dead volume requirement of the closed reservoir, many repetitive aspirate/dispense functions are required. In many applications it requires appreciably more time to rinse the flow passages than the productive time.

Another impediment, with washing in this mode, is clogging of the ink jet solenoid valve due to particulate matter in the fluid stream. On the dispense function, particulate matter from the reservoir must pass down through the valve seat which is a very confined space. As the valve armature closes on the valve seat, any particulate matter on the valve seat is hammered into the sealing surface of the seat. This leads to premature system failure.

Accordingly, it is a principal object of the present invention to provide a pipettor head and method of use for transferring small aliquots of liquid, typically from 50 nanoliters to 5 microliters (although not limited to these volumes) from a source to a destination.

A further object of the invention is to provide such a pipettor head and method of use that minimizes dead volume.

Another object of the invention is to provide such a pipettor head and method of use that requires minimal rinsing time vs. pipetting time.

An additional object of the invention is to provide such a pipettor head that is adaptable to single or multiple channel functions.

Yet a further object of the invention is to provide such a pipettor head and method of use that provides a rinsing function that prolongs the life of the valve which is the active component of the pipettor head.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a pipettor head, comprising: a body; one or more solenoid valves disposed in said body; each said one or more solenoid valves having an outlet at a lower end and an inlet at an upper end; each said one or more solenoid valves having said outlet attached to a dispensing passageway; each said one or more solenoid valves having said inlet attached to a standpipe; and said standpipe having an open top communicating with an interior of a closed vacuum/pressure chamber defined in said pipettor head, said closed vacuum/pressure chamber being arranged such that vacuum or pressure may be selectively applied to said closed vacuum/pressure chamber. A method of using said pipettor head is also provided.

BRIEF DESCRIPTION OF THE DRAWING

Understanding of the present invention and the various aspects thereof will be facilitated by reference to the accompanying drawing figures, provided for purposes of illustration only and not intended to define the scope of the invention, on which.

DETAILED DESCRIPTION OF THE PREFERRED EMBODIMENTS

Figure 1:
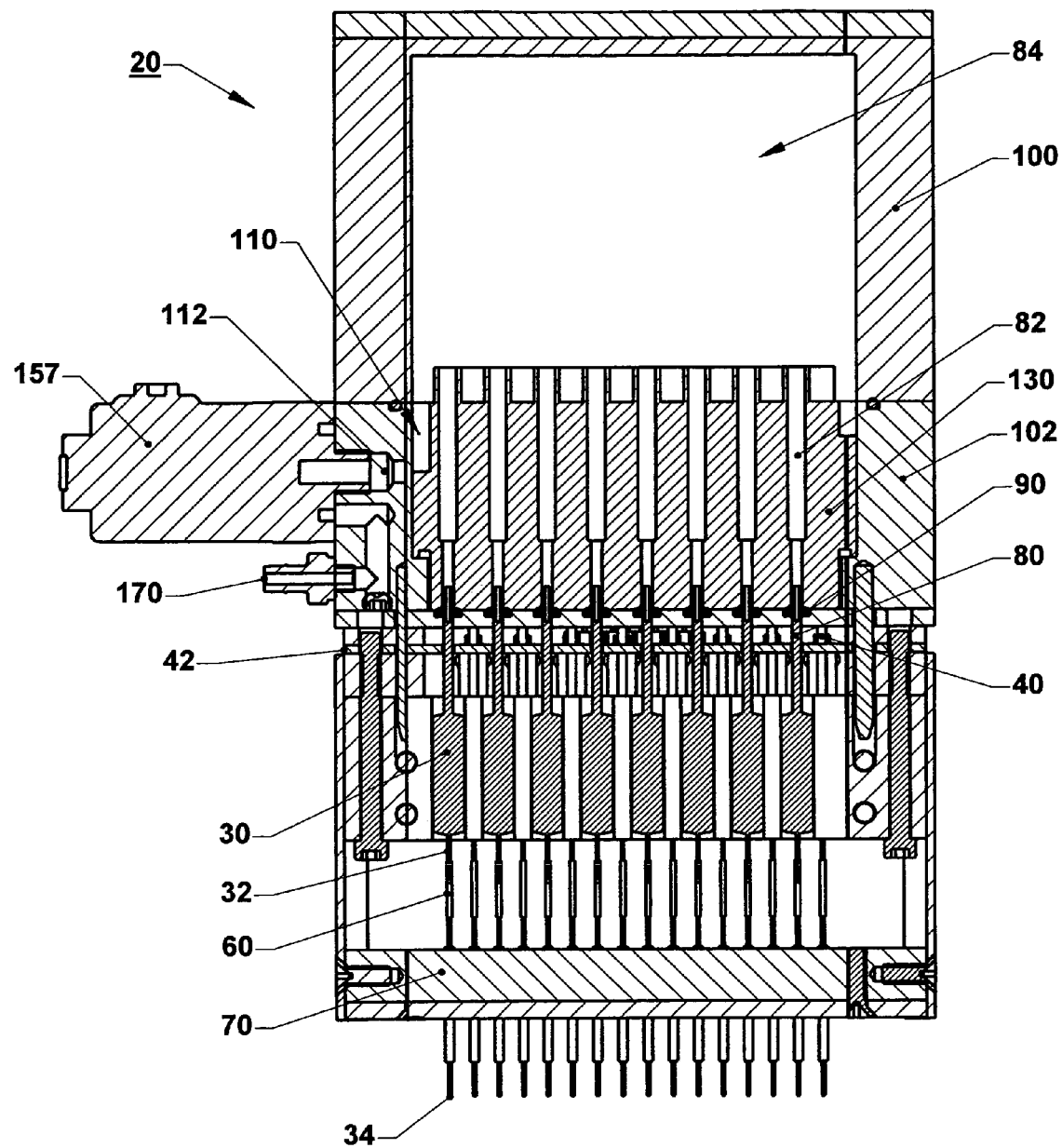
FIG. 1 is a front elevational view, partially cut-away, of a pipettor head constructed according to the present invention.

In general, the invention modifies the reservoir on the inlet side of the valve. Commonly, this is a closed reservoir that is evacuated or pressurized to aspirate or dispense, respectively. The invention replaces that closed reservoir with multiple standpipes that are open to the atmosphere of a closed chamber. The invention can provide multiple but independent liquid reservoirs to which a common atmosphere, positive or negative pressure, can be applied.

Each standpipe is volumetrically sized to contain the maximum volume the system can deliver on the dispense function prior to refilling with an aspirate function. To wash the flow paths between functions, a negative pressure is applied to the standpipes through the vacuum/pressure chamber. The control valve opens, creating a negative pressure at what is normally the output orifice. Immersing this orifice in a wash solution will cause flow up through the control valve to fill the standpipe. When the maximum volume of the standpipe is reached, it will overflow into the surrounding chamber.

The volume of the standpipe determines the maximum volume to be dispensed from one filling. This could be one dispense per fill or multiple dispenses per fill. The minimum volume to fill the system is the volume of the flow path between the delivery orifice and the inlet side of the valve seat, plus the desired delivery volume. Thus, the dead volume or non-usable volume on each aspiration, is that volume between the valve seat and delivery orifice. This can be held very small. This dead volume is critical when handling precious reagents, e.g., antibodies grown in mice or reagents produced by polymer chain reactions (PCR), for example.

By using higher vacuum on the wash cycle, than on the normal aspirate function, say thirty inches of mercury vs. five inches of mercury for the dispensing function, a faster, more efficient wash function is achieved. Thus, wash fluid overflows the standpipe into the surrounding chamber which is evacuated to a vacuum trap within the vacuum source line. The vacuum trap separates the liquid from the flow.

The direction of the flow of the wash solution is reversed from the normal dispense direction. This means any particulate matter is washed up away from the valve seat and not down into that restricted area. The smallest orifice in the system is at the delivery orifice. The wash cycle of this invention puts that restriction at the inlet instead of the outlet. Thus, it acts as an inlet filter instead of an outlet restriction during the wash cycle. The net result is a faster, more efficient wash cycle that prolongs the life and reliability of the system.

The present invention is described by reference to a sixteen needle pipettor, but it is applicable as well to a single function pipettor as well as to multiple function pipettors of numbers of needles other than sixteen. The invention is also application to ranges of liquid aspirated and dispensed in addition to that noted.

Reference should now be made to the drawing figures on which similar or identical elements are given consistent identifying numerals throughout the various figures thereof, and on which parenthetical references to figure numbers, when used, direct the reader to the view(s) on which the element(s) being described is (are) best seen, although the element(s) may be seen on other figures also.

FIG. 1 illustrates a pipettor head, constructed according to the present invention, and generally indicated by the reference numeral 20. Pipettor head 20 includes sixteen fast acting, electrical operated, micro fluidic solenoid valves, as at 30, disposed in two rows of eight (only one row shown on FIG. 1) each having a dispensing flow passage, as at 32, depending from the bottom thereof, and terminating at its distal end in a small output orifice 34. Output orifice 34 is normally a sapphire jewel orifice with a 0.003 inch to 0.004 inch diameter opening. Dispensing flow passages 32 may be rigid tubing or elastomeric depending on the design parameters of the system. If lower pressures are used, the tubing can be elastomeric, for example Teflon, which is easier to connect. Higher working pressure will require a rigid connection such as stainless steel hypodermic needle tubing. Output orifices 34 are disposed in line on 4.5 millimeter center to center spacing. This spacing conforms to the well centers on a 384 well plate and meets the dimensional requirements of the Society for Biomolecular Screening (SBS) standard. Other spacings can be used as well.

Figure 2:
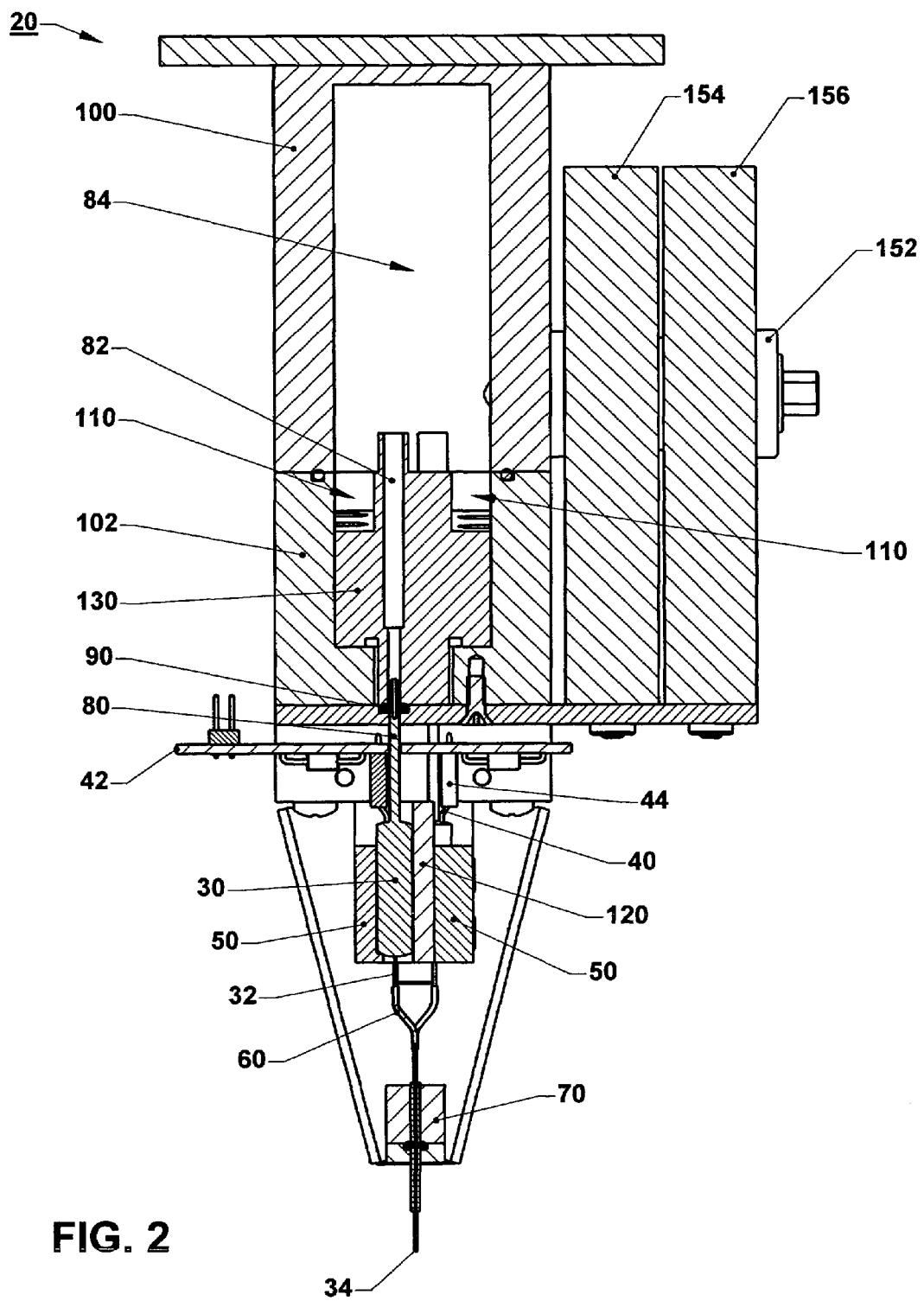
FIG. 2 is a side elevational view, partially cut-away, of the pipettor head.

Solenoid valves 30 are the active elements in the system and each is connected electrically by pins, as at 40, that frictionally plug into sockets soldered to a connecting printed circuit board 42. Solenoid valves 30 are designed to provide ease of replacement should a solenoid valve fail. The body of each valve 30 is clamped to a main support (120 on FIG. 2) by two bolted clamp bars 50 (FIG. 2). Removal of a clamp bar 50 permits a failed valve 30 to be unplugged from connecting printed circuit board 42. The connection of valves 30 to dispensing flow passages 32 is made with small pieces of elastomeric tubing, as at 60, that may be easily disconnected from the body of the valves. Dispensing flow passages 32 are secured in place by means of a support 70 fixedly disposed at the lower end of pipettor head 20.

The inlet 80 of each solenoid valve 30 extends into the bottom of its own individual Teflon standpipe 82 which has an open top communicating with a vacuum/pressure chamber 84. The bottom of each standpipe 82 is sealed to the bottom of vacuum/pressure chamber 84 and to inlet 80 by means of a seal 90 which is commonly an O-ring seal. Vacuum/pressure chamber 84 is formed by the bolting and sealing of top cover 100 to a bottom body 102, the latter two elements may be machined from Delrin. Vacuum/pressure chamber 84 is connected to a vacuum source and to a positive pressure source (neither shown) which are externally supplied to pipettor head 20. The design of standpipes 82 is such that when one overflows, the overflowing effluent cannot enter an adjacent standpipe. The effluent is captured by as surrounding drain cavity 110 (FIG. 2) connected to a vacuum port 112 (FIG. 2).

For an aspirate function, the outlet orifices 34 are submerged in the liquid to be aspirated. A vacuum of approximately one to five inches of mercury is applied to vacuum/pressure chamber 84 surrounding the sixteen standpipes 82. Micro fluidic valves 30 are opened for a defined time allowing flow from the output orifices into the standpipes 82. The maximum volume that can be aspirated is determined by the internal volumes of standpipes 82 and their connecting pathways to the output orifices. Volumes in excess of this will overflow the standpipes 82 and go to waste.

For a dispense function, the vacuum on vacuum/pressure chamber 84 is replaced with a positive pressure, typically one to five psi, but it may be more depending on the application. With positive pressure applied to standpipes, flow will be out of the output orifices for the period of time micro fluidic valves 30 are open. This open time is precisely controlled by the electronic circuitry driving valves 30. Both frequency and time of opening are controlled by circuitry well known in the existing art. Controlling these factors in combination with the positive pressure determine the volume of liquid to be dispensed.

The maximum volume that can be dispensed with precision is the volume of liquid contained in the standpipes 82 down to the valve seats in the micro fluidic valves 30. If air is in the flow path between the valve seat and the delivery output orifices 34, the delivery precision will be affected by the compressibility of the air. The volume contained in the flow path between the valve seat and the orifice is the dead volume of the system. For precious liquids, this dead volume may be recovered by opening the pressurized valves 30 with the output orifices 34 disposed over a suitable collection container.

To wash the system between delivery cycles of different liquids, the delivery orifices are submerged in a suitable wash fluid. A higher vacuum, up to thirty inches of mercury, is applied to vacuum/pressure chamber 84. This creates a fast, efficient wash through the entire fluid pathway. Where feasible, this fluid pathway is made of, or coated with, hydrophobic material such as Teflon® to facilitate release of liquids. The length of time micro fluidic valves 30 are open controls the washing action. Multiple rinses with different liquids may be made as required by the application.

At the completion of the wash function, the delivery output orifices 34 are moved to free air. Vacuum/pressure chamber 84 is again switched from vacuum to positive pressure. Opening micro fluidic valves 30 under this condition will blow air through the flow passage to dry it. The system is now ready to repeat the sequence for the next set of liquids.

FIG. 2 illustrates more clearly the structure of drain cavity 110, clamping bars 50 clamping valves 30 to a main support 120, and support 70 and also illustrates connection 44 from printed circuit board 42 to a main control.

Figure 3:
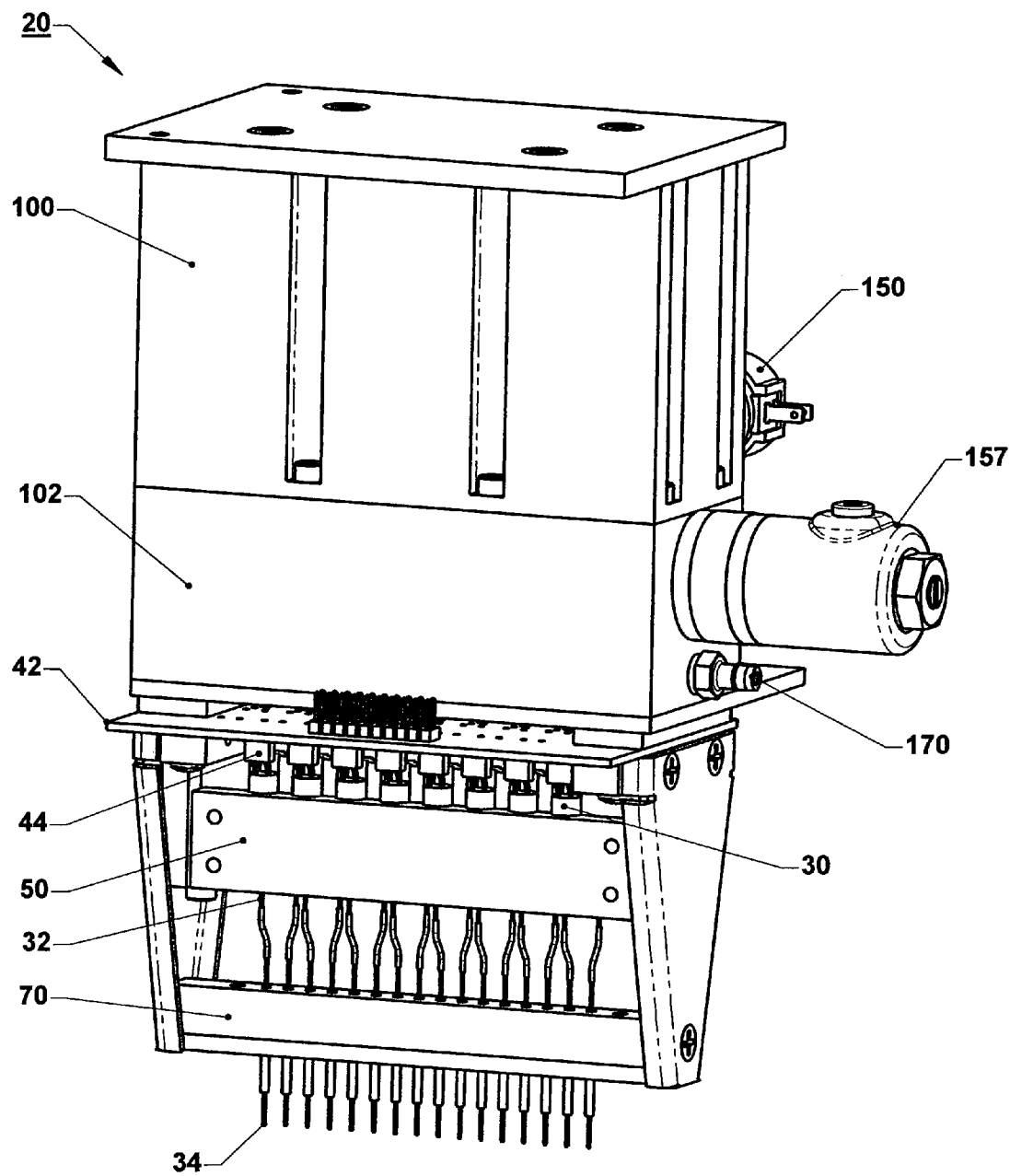
FIG. 3 is a front/left side/top isometric view of the pipettor.

FIG. 3 illustrates the elements of pipettor head 20 described above.

Figure 4:
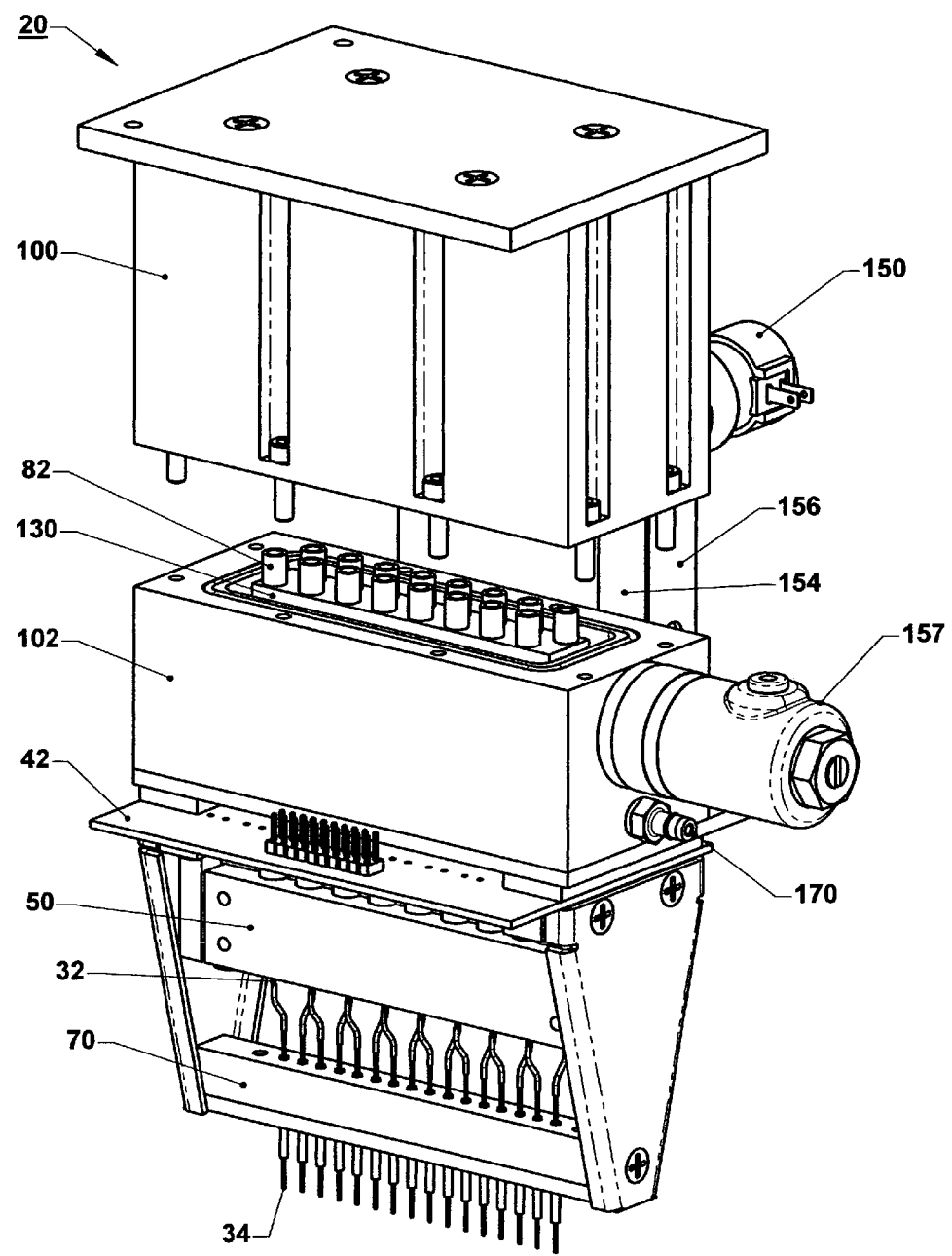
FIG. 4 is a front/right side/top isometric view of the pipettor, with the vacuum/pressure chamber spaced apart from rest of the pipettor.

FIG. 4 illustrates the elements of pipettor head 20 described above and further illustrates that standpipes 82 may be formed in an insert 130 of polymeric material, for example Teflon® material, inserted in a cavity formed in bottom body 102 which may be formed of Delrin®.

Figure 5:
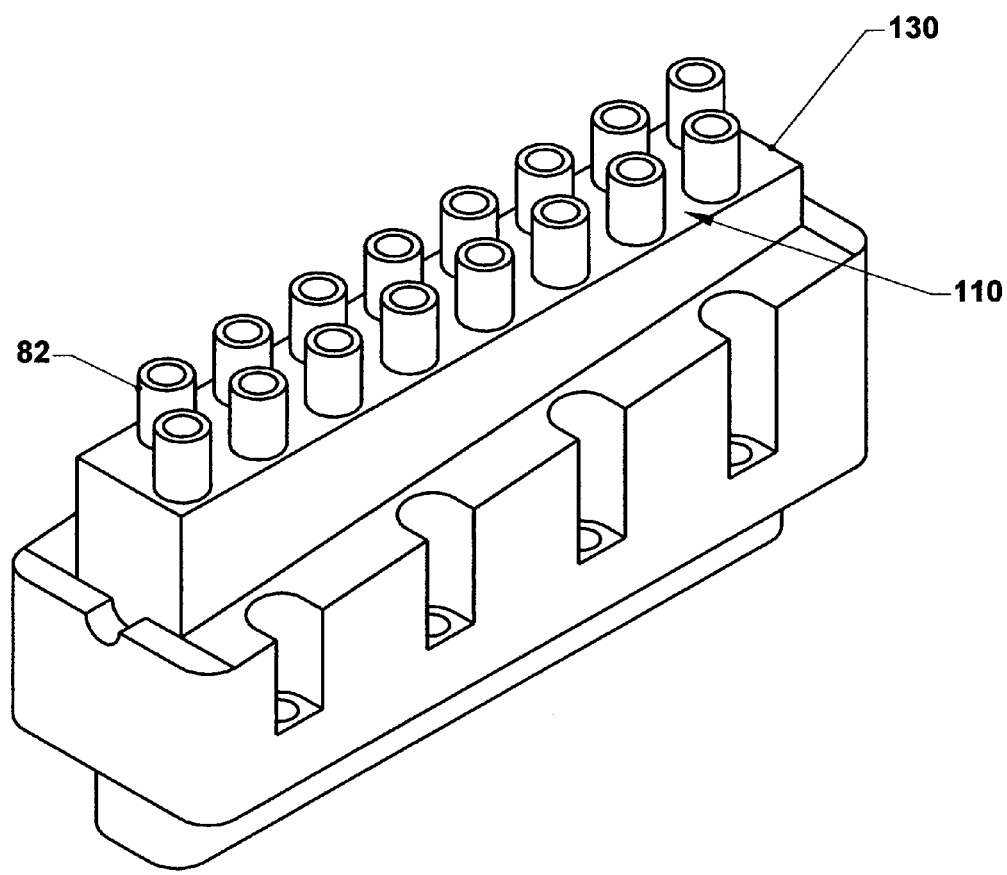
FIG. 5 is a front/left side/top isometric view of an insert containing sixteen standpipes.

FIG. 5 more clearly illustrates the structure of insert 130 (FIG. 4) and illustrates that there are four bolt holes along one side of the insert for securing insert 130 in bottom body 102. Another four bolt holes (not shown) are disposed on the opposite side of insert 130.

Figure 6:
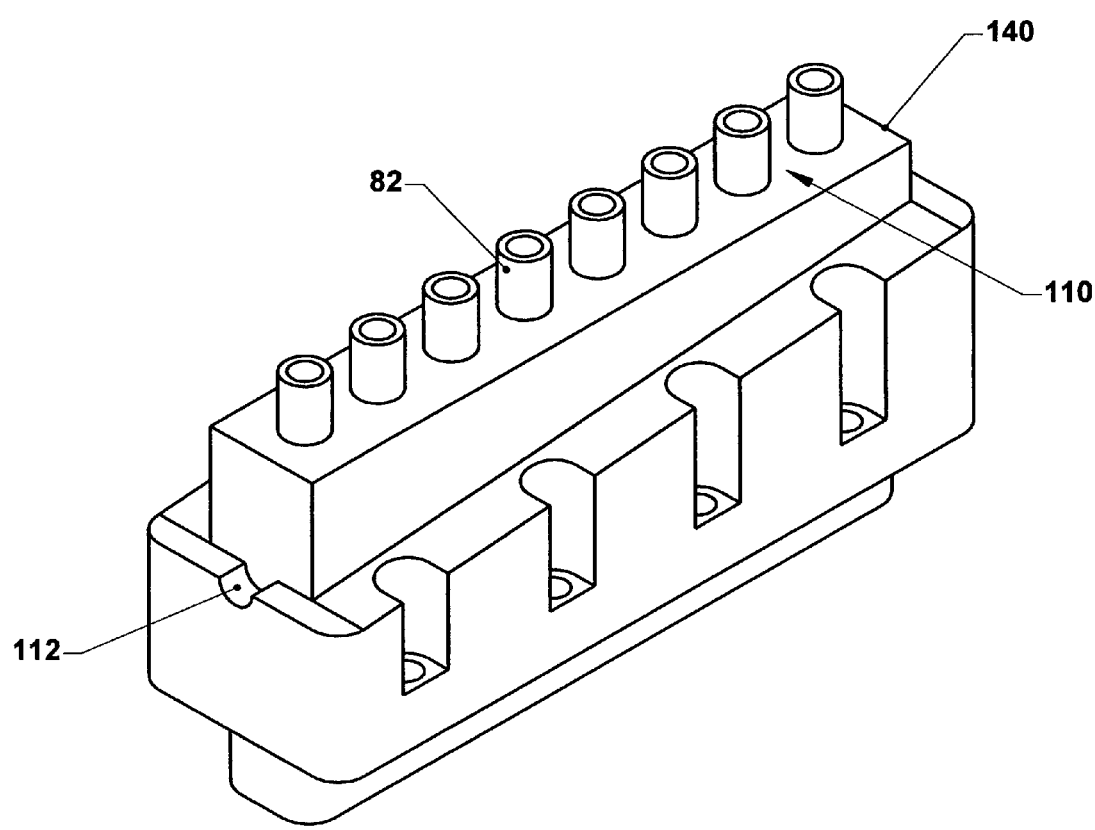
FIG. 6 is a front/left side/top isometric view of an insert containing eight standpipes.

FIG. 6 illustrates an eight position insert 140.

Figure 7:
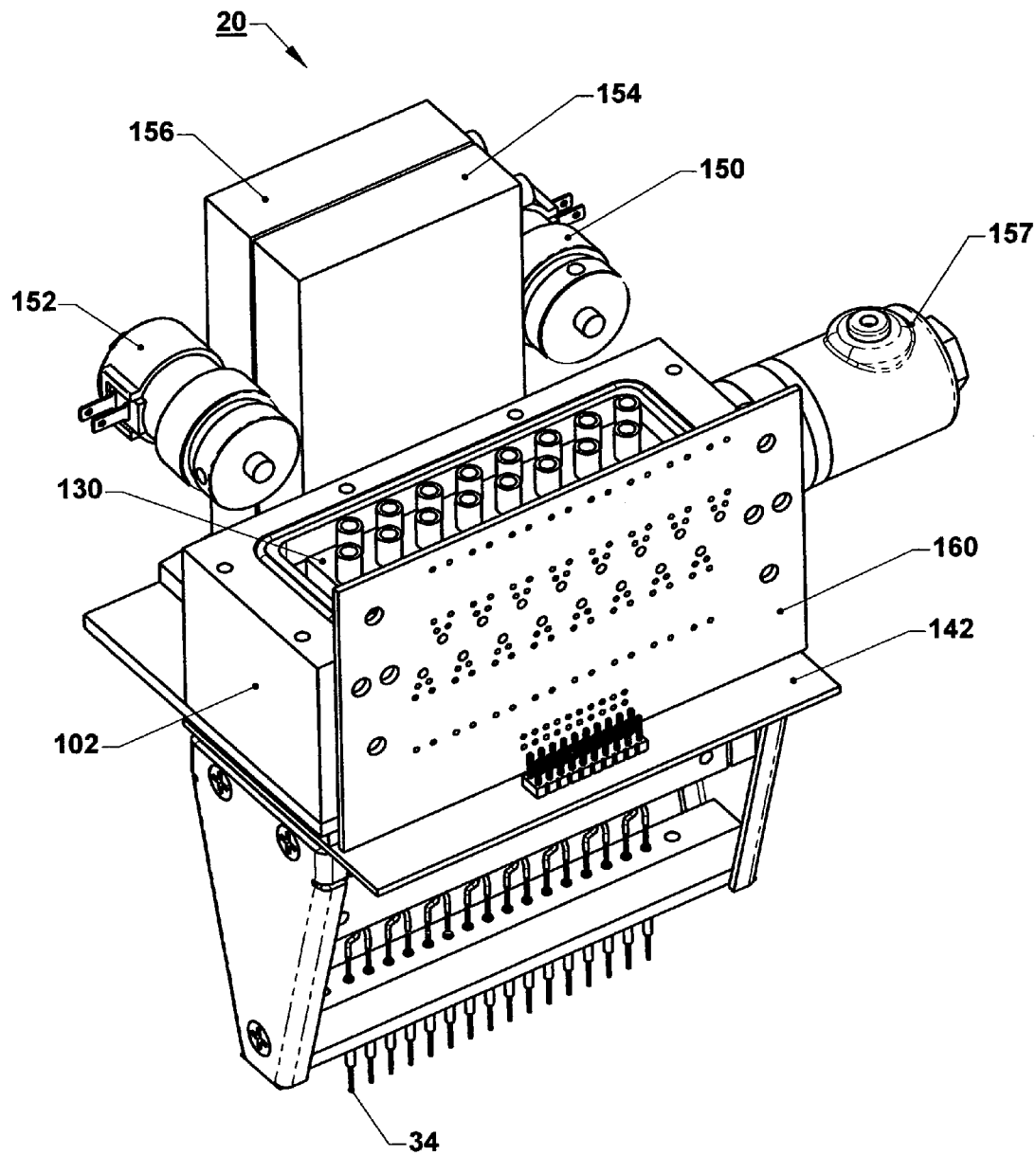
FIG. 7 is a rear/right side/top isometric view of the pipettor, with the vacuum and pressure valves spaced from the rest of the pipettor and with the vacuum/pressure chamber removed.

FIG. 7 illustrates pipettor head 20 with cover 100 removed and, in addition to the elements described above, illustrates a vacuum valve 150, a pressure valve 152, a vacuum regulator 154, a pressure regulator 156, a drain solenoid valve 157, and a main control printed circuit board 160.

Figure 8:
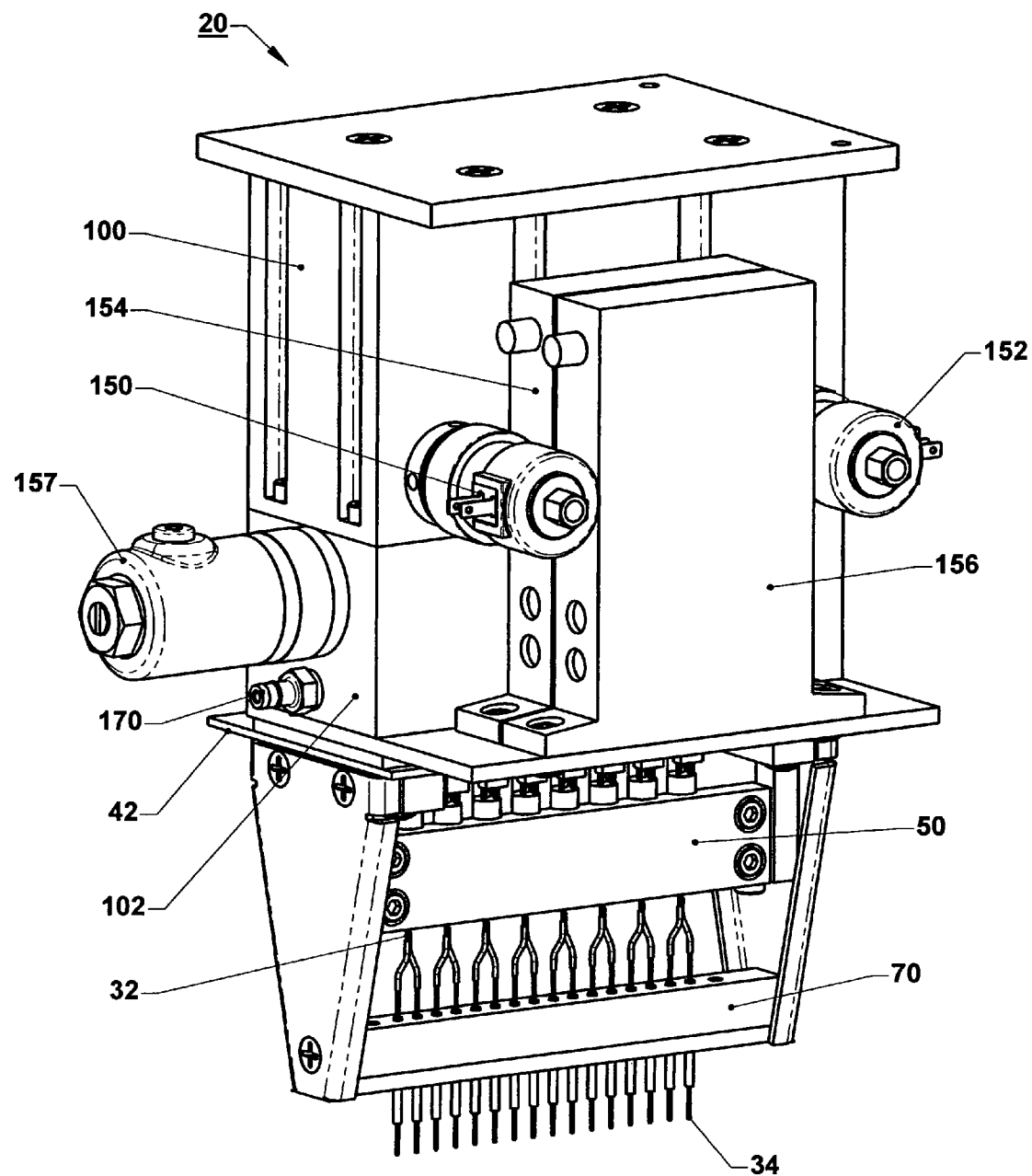
FIG. 8 is a front/right side/top isometric view of the pipettor.
Figure 9:
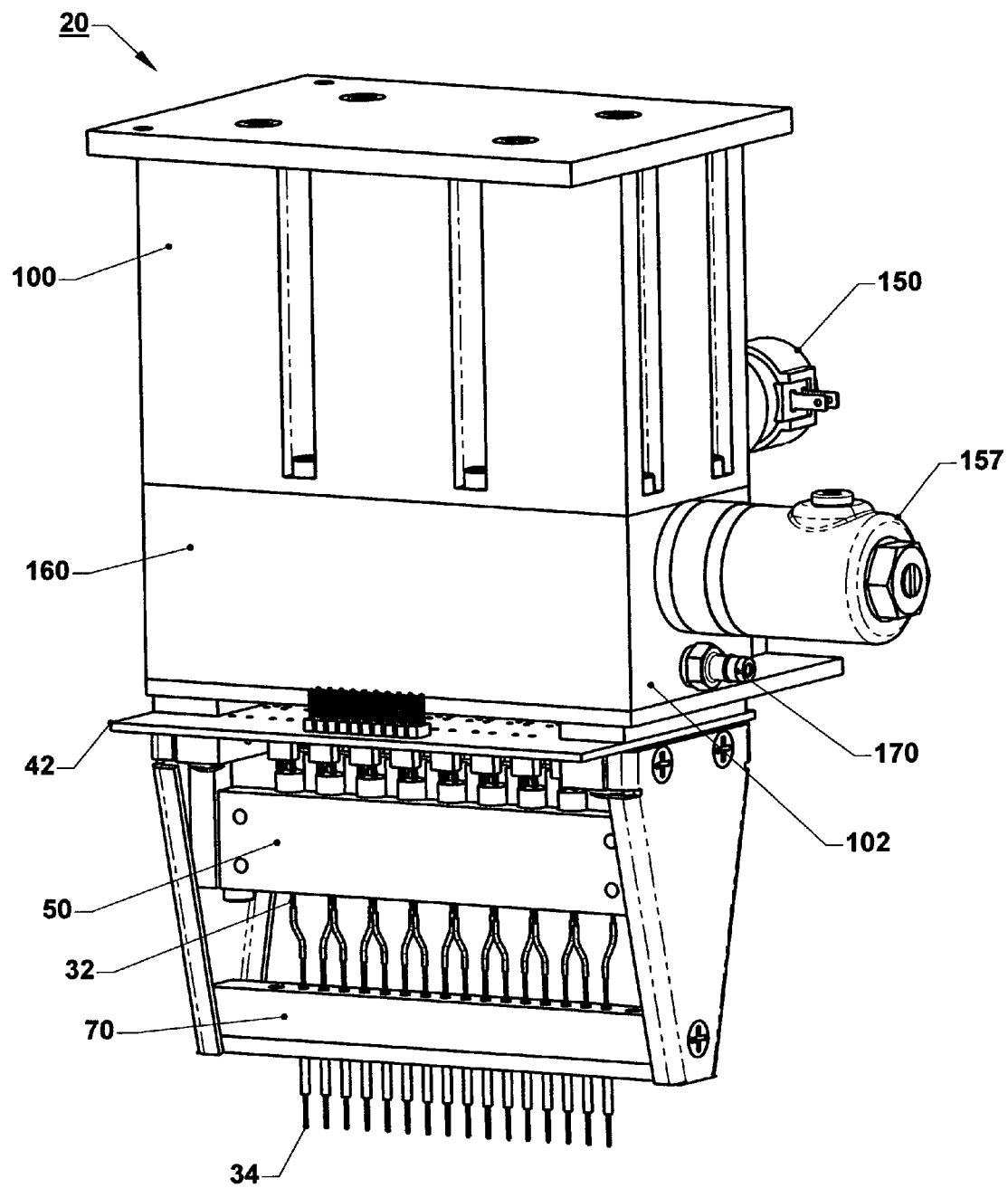
FIG. 9 is a rear/left side/top isometric view of the pipettor.

FIGS. 8 and 9 illustrate pipettor head 20 and reference the elements described on FIG. 7 and also illustrate drain opening 170 in bottom body 102 (FIG. 4).

In the embodiments of the present invention described above, it will be recognized that individual elements and/or features thereof are not necessarily limited to a particular embodiment but, where applicable, are interchangeable and can be used in any selected embodiment even though such may not be specifically shown.

Spatially orienting terms such as "above", "below", "upper", "lower", "inner", "outer", "inwardly", "outwardly", "vertical", "horizontal", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

The invention claimed is:

1. A pipettor head, comprising:
   (a) a body;
   (b) one or more solenoid valves disposed in said body;
   (c) each said one or more solenoid valves having an outlet at a lower end and an inlet at an upper end;
   (d) each said one or more solenoid valves having said outlet attached to a dispensing passageway;
   (e) each said one or more solenoid valves having said inlet attached to a standpipe; and
   (f) said standpipe having an open top communicating with an interior of a closed vacuum/pressure chamber defined in said pipettor head, said closed vacuum/pressure chamber being arranged such that vacuum or pressure may be selectively applied to said closed vacuum/pressure chamber.

2. A pipettor head, as defined in claim 1, wherein: said one or more solenoid valves comprise at least two valves each connected to a standpipe and said standpipes are arranged such that overflow from one said standpipe cannot enter another said standpipe.

3. A pipettor head, as defined in claim 1, wherein: said dispensing passageway terminates at its distal end in an orifice having a diameter smaller than said dispensing passageway.

4. A pipettor head, as defined in claim 2, wherein: said orifice has a diameter from about 0.003 to about 0.004-inch.

5. A pipettor head, as defined in claim 1, wherein: pressure above atmospheric pressure is applied to said vacuum/pressure chamber to assist in dispensing liquid from said standpipe.

6. A pipettor head, as defined in claim 1, wherein: a vacuum below atmospheric pressure is applied to said vacuum/pressure chamber to assist in aspirating liquid from said standpipe.

7. A pipettor head, as defined in claim 6, wherein: a higher vacuum, i.e., lower negative pressure, than is used to assist in aspirating is applied to said vacuum/pressure chamber to assist in washing said orifice, said dispensing passageway, said solenoid valve, said standpipe, and any interconnecting passageways.

8. A method of using a pipettor head, comprising: providing said pipettor head having: a body; one or more solenoid valves disposed in said body; each said one or more solenoid valves having an outlet at a lower end and an inlet at an upper end; each said one or more solenoid valves having said outlet attached to a dispensing passageway; each said one or more solenoid valves having said inlet attached to a standpipe; and said standpipe having an open top communicating with an interior of a closed vacuum/pressure chamber defined in said pipettor head, said closed vacuum/pressure chamber being arranged such that vacuum or pressure may be selectively applied to said closed vacuum/pressure chamber; said method comprising: applying pressure to said vacuum/pressure chamber to assist in dispensing liquid from said standpipe or applying vacuum to assist in filling said standpipe.

9. A method of using a pipettor head, as defined in claim 8, further comprising: providing said one or more solenoid valves comprising at least two valves each connected to a standpipe and said standpipes are arranged such that overflow from one said standpipe cannot enter another said standpipe.

10. A method of using a pipettor head, as defined in claim 8, further comprising: providing said dispensing passageway terminating at its distal end in an orifice having a diameter smaller than said dispensing passageway.

11. A method of using a pipettor head, as defined in claim 10, further comprising: providing said orifice having a diameter from about 0.003 to about 0.004-inch.

12. A method of using a pipettor head, as defined in claim 8, further comprising: applying pressure above atmospheric pressure to said vacuum/pressure chamber to assist in dispensing liquid from said standpipe.

13. A method of using a pipettor head, as defined in claim 8, further comprising applying vacuum below atmospheric pressure to said vacuum/pressure chamber to assist in aspirating liquid to fill said standpipe.

14. A method of using a pipettor head, as defined in claim 8, further comprising: applying vacuum to said vacuum/pressure chamber to assist in washing, in order, said orifice, said dispensing passageway, said solenoid valve, and said standpipe.

* * * * *